United States Patent
Koh et al.

(10) Patent No.: US 10,601,068 B2
(45) Date of Patent: Mar. 24, 2020

(54) ELECTROLYTE FOR LITHIUM SECONDARY BATTERY AND LITHIUM SECONDARY BATTERY COMPRISING SAME

(71) Applicant: Samsung SDI Co., Ltd., Yongin-si, Gyeonggi-do (KR)

(72) Inventors: Joo Hwan Koh, Seuol (KR); Jong Ho Jeon, Daejeon (KR); Jin Hee Kim, Suwon-si (KR); Sung Nim Jo, Seoul (KR); Tae Hwan Yu, Seoul (KR); Jung Joo Cho, Hwaseong-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 166 days.

(21) Appl. No.: 15/538,960

(22) PCT Filed: Jul. 27, 2015

(86) PCT No.: PCT/KR2015/007787
§ 371 (c)(1),
(2) Date: Jun. 22, 2017

(87) PCT Pub. No.: WO2016/104903
PCT Pub. Date: Jun. 30, 2016

(65) Prior Publication Data
US 2017/0358814 A1    Dec. 14, 2017

(30) Foreign Application Priority Data
Dec. 22, 2014    (KR) .......................... 10-2014-0185907

(51) Int. Cl.
*H01M 10/052*     (2010.01)
*H01M 10/0567*   (2010.01)
(Continued)

(52) U.S. Cl.
CPC ..... *H01M 10/052* (2013.01); *H01M 10/0567* (2013.01); *C01D 15/005* (2013.01);
(Continued)

(58) Field of Classification Search
CPC ........... H01M 10/052; H01M 10/0567; H01M 10/0568; H01M 6/16
See application file for complete search history.

(56) References Cited

U.S. PATENT DOCUMENTS

| | | | |
|---|---|---|---|
| 4,216,192 A |   | 8/1980 | Rao et al. |
| 5,532,082 A | * | 7/1996 | Saidi ...................... H01M 4/12 429/306 |

(Continued)

FOREIGN PATENT DOCUMENTS

| | | |
|---|---|---|
| CN | 101079511 A | 11/2007 |
| CN | 101765939 A | 6/2010 |

(Continued)

OTHER PUBLICATIONS

EPO Extended Search Report dated Jul. 17, 2018, for corresponding European Patent Application No. 15873431.9 (9 pages).

(Continued)

*Primary Examiner* — Kenneth J Douyette
(74) *Attorney, Agent, or Firm* — Lewis Roca Rothgerber Christie LLP

(57) ABSTRACT

Provided are an electrolyte for a lithium secondary battery and a lithium secondary battery including the electrolyte, wherein the electrolyte further includes a solid salt as an additive, wherein the solid salt contains one type of cation selected from ammonium-based cations and a thiocyanate anion ($SCN^-$). According an embodiment, the lithium secondary battery may have improved life characteristics by providing the electrolyte containing the additive.

6 Claims, 1 Drawing Sheet

(51) Int. Cl.
- *H01M 10/0568* (2010.01)
- *C01D 15/00* (2006.01)
- *C07C 69/01* (2006.01)
- *C07C 211/63* (2006.01)
- *C07C 301/00* (2006.01)
- *C07C 305/00* (2006.01)

(52) U.S. Cl.
CPC ............ *C07C 69/01* (2013.01); *C07C 211/63* (2013.01); *C07C 301/00* (2013.01); *C07C 305/00* (2013.01); *H01M 10/0568* (2013.01); *H01M 2300/0025* (2013.01)

(56) References Cited

U.S. PATENT DOCUMENTS

| | | | |
|---|---|---|---|
| 2003/0170546 A1* | 9/2003 | Boon | G01N 27/4073 429/317 |
| 2004/0002002 A1* | 1/2004 | Mizuta | H01G 9/035 429/188 |
| 2004/0053129 A1 | 3/2004 | Jung et al. | |
| 2007/0042266 A1 | 2/2007 | Oh et al. | |
| 2010/0304225 A1 | 12/2010 | Pascaiy et al. | |
| 2011/0206979 A1 | 8/2011 | Giroud et al. | |
| 2017/0358814 A1 | 12/2017 | Koh et al. | |

FOREIGN PATENT DOCUMENTS

| | | |
|---|---|---|
| CN | 102138235 A | 7/2011 |
| EP | 1906481 A1 | 4/2008 |
| JP | 1-262617 | 10/1989 |
| JP | 5-13088 A | 1/1993 |
| JP | 2002-25607 A | 1/2002 |
| KR | 10-0467453 B1 | 1/2005 |
| KR | 10-0751203 B1 | 8/2007 |
| KR | 10-2008-0032326 A | 4/2008 |
| KR | 10-2010-0051794 A | 5/2010 |
| KR | 10-2012-0011209 A | 2/2012 |
| KR | 10-1264435 B1 | 5/2013 |
| WO | WO 2006/088304 A1 | 8/2006 |

OTHER PUBLICATIONS

Chinese Office Action, with English translation, dated Jan. 30, 2019 for corresponding CN Application No. 201580076690.1 (15 pages).
Chinese Patent Second Office Action with English Translation for corresponding Chinese Patent Application No. 201580076690.1, dated Sep. 4, 2019, 14 pages.

* cited by examiner

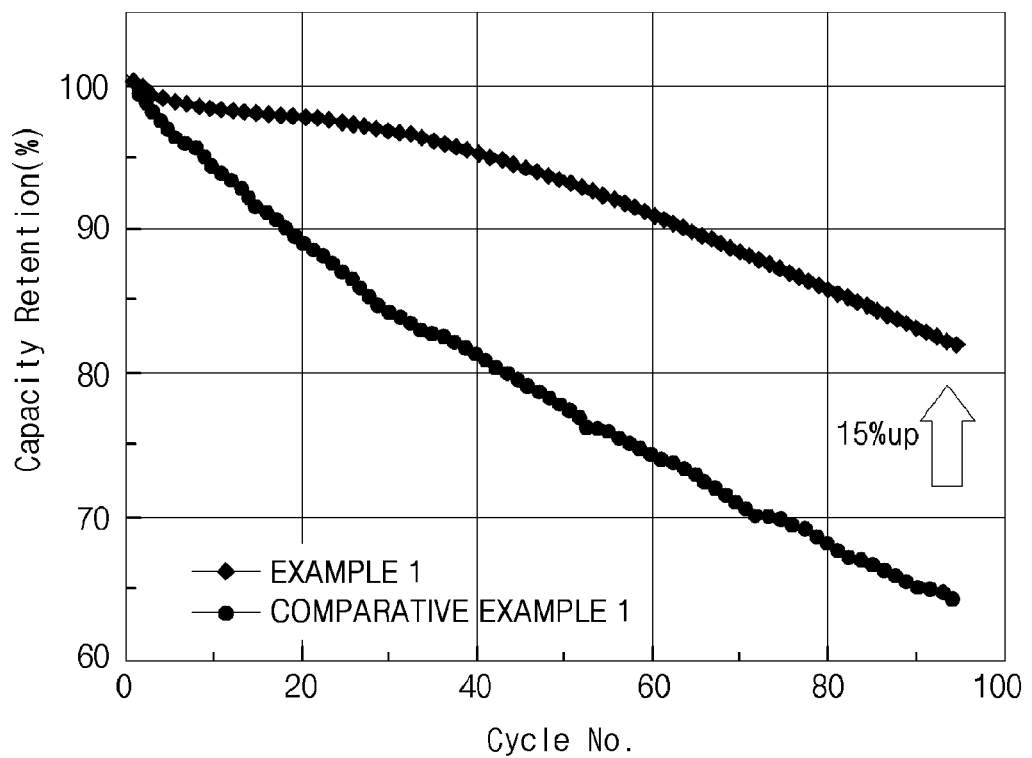

ELECTROLYTE FOR LITHIUM SECONDARY BATTERY AND LITHIUM SECONDARY BATTERY COMPRISING SAME

CROSS-REFERENCE TO RELATED APPLICATION(S)

This application is a National Phase Patent Application of International Patent Application Number PCT/KR2015/007787, filed on Jul. 27, 2015, which claims priority of Korean Patent Application 10-2014-0185907, filed Dec. 22, 2014. The entire contents of both of which are incorporated herein by reference.

TECHNICAL FIELD

One or more embodiments relate to an electrolyte for a lithium secondary battery device and a lithium secondary battery including the electrolyte, or, more particularly, to a lithium secondary battery device and a lithium secondary battery including the electrolyte that may improve life characteristics of a battery.

BACKGROUND ART

According to technological development and increased demand for mobile devices, demand for using secondary batteries as energy sources has rapidly increased. Among such secondary batteries, lithium secondary batteries having high energy density and operating potential, long cycle life, and low self-discharge rate are commercially available and widely used.

A lithium secondary battery has a structure in which an electrode assembly including a positive electrode, a negative electrode, and a porous separator disposed between the positive electrode and the negative electrode is impregnated in an electrolyte including a lithium salt, wherein the positive electrode and the negative electrode are each prepared by applying an active material on an electrode current collector. During a charging process, lithium ions of a positive active material are dissolved and intercalated into an active material layer of the negative electrode. During a discharge process, lithium ions in the active material layer are dissolved and intercalated into the positive active material. The electrolyte serves as a medium that transfers lithium ions between the negative electrode and the positive electrode.

The electrolyte generally includes an organic solvent and an electrolyte salt. For example, the electrolyte may be prepared by adding a lithium salt, such as $LiPF_6$, $LiBF_4$, or $LiClO_4$, in a solvent mixture including high-dielectric cyclic carbonate, such as propylene carbonate or ethylene carbonate; and low-viscosity chain carbonate, such as diethyl carbonate, ethyl methyl carbonate, or dimethyl carbonate.

Since a lithium-containing halide salt such as a lithium-containing fluoride salt or a lithium-containing chloride salt that is generally used as an electrolyte salt sensitively reacts with water, the lithium-containing halide salt reacts with water during a preparation process of a battery or in a battery and thus produces HX (X=F, Cl, Br, I), which is a type of strong acid. Particularly, since a lithium salt, $LiPF_6$, is unstable at a high temperature, its anion may be thermally decomposed, and thus an acidic material such as HF may be produced. When the acidic material exists in a battery, it unconditionally brings along undesired side reactions.

For example, a solid electrolyte interface (SEI) layer on a negative electrode surface may easily break due to high reactivity of the HX (X=F, Cl, Br, I), which induces continuous regeneration of the SEI layer, and thus an increase in interface resistance of a negative electrode may result due to an increase in a layer amount of the negative electrode. Also, due to positive electrode surface adsorption of lithium fluoride (LiF), which is a by-product of formation of hydrofluoric acid (HF), a positive electrode interface resistance may increase. Further, the HX may generate sudden oxidation in the battery which may dissolve or degrade positive and negative active material. Particularly, when a transition metal cation included in a lithium metal oxide, which is used as a positive active material, is dissolved, an additional negative electrode film may be formed as the cation electrodeposits on the negative electrode, which may thus result in a further increase in the negative electrode resistance.

The SEI layer is formed on a negative electrode surface when a carbonate-based polar non-aqueous solvent reacts with lithium ions in an electrolyte during an initial charging process of a lithium secondary battery. The SEI layer suppresses decomposition of the carbonate-based electrolyte on the negative electrode surface and thus serves as a protecting layer that stabilizes the battery. However, the SEI layer that is only formed by using an organic solvent and a lithium salt is somewhat insufficient to serve as a continuous protecting layer, and thus the SEI layer may be slowly destroyed by increased electrochemical energy and thermal energy when charging/discharging of the battery continues or when a fully-charged battery is stored at a high temperature. Then, a side reaction of decomposition caused by reaction between a negative active material surface exposed by the destruction of the SEI layer and an electrolyte solvent may continuously occur, and thus a resistance of the negative electrode may increase.

In addition to the cause described above, an interface resistance between an electrode and an electrolyte may increase due to various factors, and when the interface resistance increases, the performance of a battery such as a charge/discharge efficiency and life characteristics may generally deteriorate.

In order to resolve such problems, Patent Document 1 (JP1993-13088) discloses a method of improving a resistance of a lithium secondary battery by including vinylene carbonate (VC) in an electrolyte. However, a thin layer prepared by using the method still exhibits high resistance, and thus the method does not produce sufficient effects in terms of suppressing a resistance increase of a battery.

Also, Patent Document 2 (KR-2012-0011209) discloses an electrolyte solution for a lithium secondary battery including alkylene sulfate having a predetermined structure, an ammonium compound having a predetermined structure, and vinylene carbonate. According to this method, an SEI layer prepared by using the sulfate-based compound is advantageous as a resistance of the SEI layer is small and thus may improve low-temperature output characteristics of the battery, but the method cannot significantly improve life characteristics of the battery, and thus further improvement is needed.

PRIOR ART

Patent Document (Patent Document 1) JP 1993-13088
(Patent Document 2) KR2012-0011209 A

DETAILED DESCRIPTION OF THE INVENTION

Technical Problem

According to an embodiment, provided is an electrolyte for a lithium secondary battery that may improve life characteristics by including a solid salt as an additive, wherein the solid salt contains an ammonium-based cation and a thiocyanate anion ($SCN^-$).

According to another embodiment, provided is a lithium secondary battery including the electrolyte.

Technical Solution

According to an embodiment, an electrolyte for a lithium secondary battery includes a lithium salt and an organic solvent, wherein the electrolyte further includes a solid salt containing an ammonium-based cation represented by Formula 1 and a thiocyanate anion ($SCN^-$).

[Formula 1]

In Formula 1, $R_1$ to $R_4$ are each independently a hydrogen, a halogen, or a C1-C8 alkyl group.

Preferably, an amount of the solid salt may be in a range of 0.01 parts to 5 parts by weight based on 100 parts by weight as the total weight of the lithium salt and the organic solvent.

Also, the solid salt may be at least one selected from the group consisting of ammonium thiocyanate, tetramethylammonium thiocyanate, tetraethylammonium thiocyanate, tetrapropylammonium thiocyanate, tetrabutylammonium thiocyanate, tetrapentylammonium thiocyanate, tetrahexylammonium thiocyanate, tetraheptylammonium thiocyanate, ethyltrimethylammonium thiocyanate, triethylmethylammonium thiocyanate, butyltrimethylammonium thiocyanate, diethyldimethylammonium thiocyanate, and dibutyldimethylammonium thiocyanate.

According to another embodiment, provided is a lithium secondary battery including the electrolyte.

Advantageous Effects of the Invention

According to one or more embodiments, a lithium secondary battery may have improved life characteristics by using an electrolyte for a lithium secondary battery, the electrolyte including a solid salt as an additive, wherein the solid salt contains an ammonium-based cation and a thiocyanate anion ($SCN^-$).

In particular, when a metal-based material, such as silicon (Si) or tin (Sn), which is a high-capacity material, is used as a negative active material, an irreversible capacity decreases significantly, and thus the effect of improving life characteristics may be significant.

DESCRIPTION OF THE DRAWINGS

FIG. 1 is a graph that compares life characteristics of lithium secondary batteries prepared by using electrolytes of Example 1 and Comparative Example 1.

BEST MODE

According to an embodiment, provided is an electrolyte for a lithium secondary battery, the electrolyte including a lithium salt and an organic solvent, wherein the electrolyte further includes a solid salt containing an ammonium-based cation represented by Formula 1 and a thiocyanate anion ($SCN^-$).

[Formula 1]

In Formula 1, R1 to R4 are each independently a hydrogen, a halogen, or a C1-C8 alkyl group.

Performance of a battery largely depends on a basic electrolyte composition and a solid electrolyte interface (SEI) layer that is produced by a reaction between an electrolyte and an electrode.

An SEI layer refers to a thin layer that is formed on a negative electrode interface as a result of a reaction between an electrolyte and a negative electrode when lithium ions migrate and intercalate into the negative electrode, wherein the lithium ions are deintercalated from a positive electrode during an initial charging process of a lithium secondary battery. The SEI layer selectively permeates lithium ions only and thus prevents organic solvents of an electrolyte having a large molecular weight that move along with the lithium ions from intercalating together into a negative electrode, which destroys a structure of the negative electrode. Also, the SEI layer prevents a side reaction between lithium ions and other materials that may occur while a charging/discharging process continues. However, an SEI layer conventionally formed by using an organic solvent and a fluoride salt or an inorganic salt is weak and porous, and thus the SEI layer is not closely densed and thus may not provide the functions described above.

Particularly, when a metal-based material, such as silicon (Si) or tin (Sn) that are a high-capacity material, is used as a negative active material, volume change that occurs during a charge/discharge process may be large, which may result in severe cracks in a surface thereof as the number of charging/discharging cycles increases, and thus the negative active material may be differentiated. During this process, as destruction and regeneration processes of an SEI layer on a negative electrode interface actively proceed, lithium may be consumed, and thus irreversible capacity may increase and the cycle life may significantly decrease.

On the other hand, the solid salt included as an additive in the electrolyte according to an embodiment has a low reduction potential, compared to that of a carbonate-based electrolyte solvent, and thus the solid salt may be reduced on a surface of a negative electrode material before the electrolyte solvent reduces during an initial charging process of a battery, which may result in formation of a firm and densed SEI layer. Therefore, co-intercalation of the electrolyte solvent into a negative active material layer or dissociation of the electrolyte solvent at a negative electrode interface resulting participation of the electrolyte into a side reaction such as an SEI layer regeneration may be prevented, and thus charge/discharge efficiency of the battery may improve.

In addition, the SEI layer thus formed is a passivation layer that has low chemical reactivity which may exhibit high stability despite long-term cycles, and thus long life characteristics may be obtained.

An amount of the solid salt is preferably in a range of 0.01 parts to 5 parts by weight, or, more preferably, may be in a range of 0.1 parts to 3.0 parts by weight, based on 100 parts by weight as the total weight of the lithium salt and the organic solvent.

When the amount is less than 0.01 parts by weight, it may be difficult to obtain the effect of forming an SEI layer having excellent stability, and when the amount is greater than 5.0 parts by weight, charge/discharge efficiency may deteriorate.

Examples of the solid salt according to an embodiment may be selected from the group consisting of ammonium thiocyanate, tetramethylammonium thiocyanate, tetraethylammonium thiocyanate, tetrapropylammonium thiocyanate, tetrabutylammonium thiocyanate, tetrapentylammonium thiocyanate, tetrahexylammonium thiocyanate, tetraheptylammonium thiocyanate, ethyltrimethylammonium thiocyanate, triethylmethylammonium thiocyanate, butyltrimethylammonium thiocyanate, diethyldimethylammonium thiocyanate, and dibutyldimethylammonium thiocyanate, but embodiments are not limited thereto.

The lithium salt included in the electrolyte according to an embodiment may be used at a concentration in a range of 0.6 M to 2.0 M, or, more preferably, in a range of 0.7 M to 1.6 M. When the concentration of the lithium salt is lower than 0.6 M, the conductivity of the electrolyte decreases, which may result in deterioration of electrolyte performance, whereas when the concentration is higher than 2.0 M, the viscosity of the electrolyte increases, which may result in decrease in mobility of lithium ions. The lithium salts may be any lithium salt that is generally used in an electrolyte for a lithium secondary battery, and examples of an anion of the lithium salt may be one selected from the group consisting of $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$.

The organic solvent included in the electrolyte may be any organic solvent that is generally used in an electrolyte for a lithium secondary battery, and examples of the organic solvent may be ether, ester, amide, linear carbonate, or cyclic carbonate that may be used alone or as a mixture of at least two selected therefrom. The organic solvent may typically include cyclic carbonate, linear carbonate, or a carbonate compound as a mixture of cyclic carbonate and linear carbonate among these examples. Examples of the cyclic carbonate compound may be one or a mixture of at least two selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and halides thereof. Also, examples of the linear carbonate compound may typically include one or a mixture of at least two selected from the group consisting of dimethyl carbonate (DMC), diethyl carbonate (DEC), dipropyl carbonate, ethyl methyl carbonate (EMC), methyl propyl carbonate, and ethyl propyl carbonate. However, embodiments are not limited thereto.

In particular, EC and PC, which are cyclic carbonates among examples of the carbonate-based organic solvent, are organic solvents having a high viscosity and a high dielectric constant. Therefore, EC and PC easily dissociate a lithium salt in an electrolyte and thus may be preferably used. When low-viscosity and low-dielectric constant linear carbonates such as DMC and DEC are mixed with the cyclic carbonate at an appropriate ratio, an electrolyte having a high electric conductivity may be prepared and thus may be more preferably used.

Also, examples of ether among the examples of the organic solvent may include one or a mixture of at least two selected from the group consisting of dimethyl ether, diethyl ether, dipropyl ether, methyl ethyl ether, methyl propyl ether, and ethyl propyl ether, but embodiments are not limited thereto.

Also, examples of ester among the examples of the organic solvent may include one or a mixture of at least two selected from the group consisting of methyl acetate, ethyl acetate, propyl acetate, methyl propionate, ethyl propionate, propyl propionate, γ-butyrolactone, γ-valerolactone, γ-caprolactone, σ-valerolactone, and ε-caprolactone, but embodiments are not limited thereto.

The electrolyte for a lithium secondary battery according to an embodiment may further include an additive for forming a conventional SEI layer within the scope of the objective of the present invention. Examples of the additive for forming an SEI layer that may be used in an embodiment may include vinylene carbonate, vinyl ethylene carbonate, fluoroethylene carbonate, cyclic sulfite, saturated sultone, unsaturated sultone, and non-cyclic sulfone, which may be used alone or as a mixture of at least two selected therefrom, but embodiments are not limited thereto.

Examples of the cyclic sulfite may include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethylpropylene sulfite, 4,6-diethylpropylene sulfite, and 1,3-butylene glycol sulfite. Examples of the saturated sultone may include 1,3-propane sultone and 1,4-butane sultone. Examples of the unsaturated sultone may include ethene sultone, 1,3-propenesultone, 1,4-butene sultone, and 1-methyl-1,3-propene sultone. Examples of the non-cyclic sulfone may include divinylsulfone, dimethylsulfone, diethylsulfone, and methylvinyl sulfone.

The additive for forming an SEI layer may be included at an appropriate amount according to type or, for example, may be included at an amount in a range of 0.01 parts to 10 parts by weight based on 100 parts by weight of the electrolyte.

According to another embodiment, provided is a lithium secondary battery including the electrolyte.

The lithium secondary battery is prepared by injecting the electrolyte prepared according to an embodiment to an electrode assembly including a positive electrode, a negative electrode, and a separator disposed between the positive electrode and the negative electrode.

Also, the positive electrode and the negative electrode may each be prepared by, first, mixing an active material, a binder, and a conducting agent with a solvent to prepare a slurry, and then applying, drying, and pressing the slurry on a current collector such as aluminum.

The positive electrode active material may be, preferably, a lithium-containing transition metal oxide, which may be, for example, one or a mixture of at least two selected from the group consisting of $Li_xCoO_2$ (where, $0.5<x<1.3$), $Li_xNiO_2$ (where, $0.5<x<1.3$), $Li_xMnO_2$ (where, $0.5<x<1.3$), $Li_xMn_2O_4$ (where, $0.5<x<1.3$), $Li_x(Ni_aCo_bMn_c)O_2$ (where, $0.5<x<1.3$, $0<a<1$, $0<b<1$, $0<c<1$, and $a+b+c=1$), $Li_xNi_{1-y}Co_yO_2$ (where, $0.5<x<1.3$ and $0<y<1$), $Li_xCo_{1-y}Mn_yO_2$ (where, $0.5<x<1.3$ and $0\le y<1$), $Li_xNi_{1-y}Mn_yO_2$ (where, $0.5<x<1.3$ and $0<y<1$), $Li_x(Ni_aCo_bMn_c)O_4$ (where, $0.5<x<1.3$, $0<a<2$, $0<b<2$, $0<c<2$, and $a+b+c=2$), $Li_xMn_{2-z}Ni_zO_4$ (where, $0.5<x<1.3$ and $0<z<2$), $Li_xMn_{2-z}Co_zO_4$ (where, $0.5<x<1.3$ and $0<z<2$), $Li_xCoPO_4$ (where, $0.5<x<1.3$), and $Li_xFePO_4$ (where, $0.5<x<1.3$). The lithium-containing transition metal oxide may be coated with a metal, such as aluminum (Al), or a metal oxide. Also, a sulfide, a selenide, and a halide may be used in addition to the lithium-containing transition metal oxide.

Examples of the negative active material may include a carbonaceous material, lithium metal, silicon, or tin from which lithium ions may generally intercalated and deintercalated, and a metal oxide such as $TiO_2$ or $SnO_2$, which has a potential with respect to lithium that is less than 2 V, may be used. Preferably, a carbonaceous material may be used, and low-crystalline carbon and high-crystalline carbon may both be used as the carbonaceous material. Examples of the low-crystalline carbon may include soft carbon and hard carbon, and examples of the high-crystalline carbon may include natural graphite, artificial graphite, Kish graphite, pyrolytic carbon, mesophase pitch-based carbon fibers, meso-carbon microbeads, mesophase pitches, and high-temperature calcined carbon such as petroleum or coal tar pitch-derived cokes.

The binder attaches the active material to the conducting agent and fixes them on the current collector, and examples of the binder may include binders generally used in a lithium ion secondary battery such as polyvinylidene fluoride, polypropylene, carboxymethylcellulose, polyvinylpyrrolidone, tetrafluoroethylene, polyethylene (PE), polyvinyl alcohol, and styrenebutadiene rubber.

Examples of the conducting agent may include artificial graphite, natural graphite, acetylene black, Ketjen black, channel black, lamp black, thermal black, conducting fibers such as carbon fibers or metal fibers, a conducting metal oxide such as titanium oxide, and metal powders of aluminum or nickel.

Also, examples of the separator may include a single olefin such as PE (or polypropylene (PP) or an olefin complex, polyamide (PA), polyacrylonitrile (PAN), polyethylene oxide (PEO), polypropylene oxide (PPO), polyethylene glycoldiacrylate (PEGA), polytetrafluoroethylene (PTFE), polyvinylidene fluoride (PVdF), and polyvinylchloride (PVC).

Although a shape of the lithium secondary battery according to another embodiment is not limited, examples of the shape may include a cylinder using a can, a box, a pouch, or a coin.

Hereinafter, embodiments will be described in detail with reference to the following examples.

<Preparation of Electrolyte>

Example 1

Fluoroethylene carbonate, ethylene carbonate, and diethyl carbonate were mixed at a volume ratio of 25:5:70 to prepare an organic solvent. Next, $LiPF_6$, as a lithium salt, was dissolved in the organic solvent to prepare a $LiPF_6$ mixture solution having a lithium salt concentration of 1.15 M. Then, tetrabutylammonium thiocyanate, as a solid salt, was added to the mixture solution at an amount of 0.5 parts by weight based on the 100 parts by weight of the mixture solution, and thus an electrolyte was prepared.

Comparative Example 1

An electrolyte was prepared in the same manner as in Example 1, except that the solid salt was not added.

<Preparation of Battery>

$LiNi_{1/3}Co_{1/3}Mn_{1/3}O_2$ as a positive active material, PVdF as a binder, and carbon black as a conducting agent were mixed at a weight ratio of 91.5:4.4:4.1 to prepare a mixture, and the mixture was dispersed in N-methyl-2-pyrolidone to prepare a positive electrode slurry. Then, the slurry was applied on an aluminum current collector, and the current collector was dried and roll-pressed to prepare a positive electrode.

Also, silicon powder as a negative active material and polyimide as a binder were mixed at a weight ratio of 85:15 to prepare a mixture, and the mixture was dispersed in pure water to prepare a slurry. The slurry was applied on a copper current collector, and the current collector was dried and roll-pressed to prepare a negative electrode.

Subsequently, a porous polyethylene film (available from Tonen) as a separator was used together with the positive electrode and the negative electrode, and the electrolyte was injected thereto, thereby completing the manufacture of a coin cell.

<Evaluation Method>

1. Cell Formation

The coin cells prepared by using the electrolytes of Example 1 and Comparative Example 1 were left at a constant temperature of 25° C. for 12 hours, charged under conditions including a constant current of 0.5 C until a voltage was 4.3 V and a constant voltage having a terminating current of 0.05 C, and discharged under conditions including a constant current of 0.5 C until a voltage was 3.0 V by using a lithium secondary battery charger/discharger (TOSCAT-3600, available from Toyo-System Co., LTD), thereby completing a cell formation process.

2. Life Characteristics

The cell that underwent the process above was charged under conditions including a constant current of 0.5 C until a voltage was 4.3 V and a constant voltage having a terminating current of 0.05 C, and discharged under conditions including a constant current of 0.5 C until a voltage was 3.0 V. The charge/discharge test under these conditions was repeated 100 times for evaluation of life characteristics, and discharge capacity retentions are shown in FIG. 1.

Referring to FIG. 1, it was confirmed that a coin cell prepared by using the electrolyte of Example 1 had improved life characteristics, compared to those of a coin cell prepared by using the electrolyte of Comparative Example 1.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A lithium secondary battery comprising an electrolyte and a negative active material, wherein the electrolyte comprises a liquid solution comprising:
   a lithium salt; and
   an organic solvent,
   wherein the electrolyte further comprises a solid salt containing an ammonium-based cation represented by Formula 1 and a thiocyanate anion ($SCN^-$):

[Formula 1]

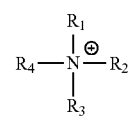

wherein, in Formula 1, $R_1$ to $R_4$ are each independently a hydrogen, a halogen, or a C1-C8 alkyl group, and wherein the negative active material comprises at least one selected from a silicon (Si)-based material, and a tin (Sn)-based material.

2. The lithium secondary battery of claim 1, wherein the solid salt is at least one selected from the group consisting of ammonium thiocyanate, tetramethylammonium thiocyanate, tetraethylammonium thiocyanate, tetrapropylammonium thiocyanate, tetrabutylammonium thiocyanate, tetrapentylammonium thiocyanate, tetrahexylammonium thiocyanate, tetraheptylammonium thiocyanate, ethyltrimethylammonium thiocyanate, triethylmethylammonium thiocyanate, butyltrimethylammonium thiocyanate, diethyldimethylammonium thiocyanate, and dibutyldimethylammonium thiocyanate.

3. The lithium secondary battery of claim 1, wherein an amount of the solid salt is in a range of 0.01 parts to 5 parts by weight based on 100 parts by weight as the total weight of the lithium salt and the organic solvent.

4. The lithium secondary battery of claim 1, wherein an anion of the lithium salt is at least one selected from the group consisting of $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2^-N^-$.

5. The lithium secondary battery of claim 1, wherein the organic solvent is at least one selected from the group consisting of ether, ester, amide, linear carbonate, and cyclic carbonate.

6. The lithium secondary battery of claim 1 further comprising at least one selected from the group consisting of vinylene carbonate, vinyl ethylene carbonate, fluoroethylene carbonate, cyclic sulfite, saturated sultone, unsaturated sultone, and non-cyclic sulfone.

\* \* \* \* \*